US008760178B2

(12) United States Patent
Rippeth (10) Patent No.: US 8,760,178 B2
(45) Date of Patent: Jun. 24, 2014

(54) METHOD FOR MEASURING TARGET COMPONENT IN ERYTHROCYTE-CONTAINING SPECIMEN (75) Inventor: John James Rippeth, Suffolk (GB)

(73) Assignee: Arkray, Inc., Kyoto (JP)

( * ) Notice: Subject to any disclaimer, the term of this patent is extended or adjusted under 35 U.S.C. 154(b) by 320 days.

(21) Appl. No.: 12/893,615

(22) Filed: Sep. 29, 2010

(65) Prior Publication Data
US 2011/0074450 A1  Mar. 31, 2011

Related U.S. Application Data (60) Provisional application No. 61/247,131, filed on Sep. 30, 2009.

(51) Int. Cl.
G01R 27/08 (2006.01)
G01N 27/02 (2006.01)
G01N 33/86 (2006.01)

(52) U.S. Cl.
USPC .............. 324/692; 324/439; 324/691; 436/70

(58) Field of Classification Search
USPC ........................................................ 324/692
See application file for complete search history.

(56) References Cited

U.S. PATENT DOCUMENTS

| | | | | |
|---|---|---|---|---|
| 4,547,735 A | * | 10/1985 | Kiesewetter et al. | 324/450 |
| 4,835,477 A | * | 5/1989 | Polaschegg et al. | 324/439 |
| 5,416,027 A | * | 5/1995 | Baudin et al. | 436/70 |
| 5,569,591 A | * | 10/1996 | Kell et al. | 435/29 |
| 5,997,817 A | * | 12/1999 | Crismore et al. | 204/403.1 |
| 6,576,117 B1 | | 6/2003 | Iketaki et al. | |
| 6,794,877 B2 | * | 9/2004 | Blomberg et al. | 324/434 |
| 7,347,926 B2 | | 3/2008 | Morita et al. | |
| 7,955,492 B2 | | 6/2011 | Fujiwara et al. | |
| 8,282,813 B2 | | 10/2012 | Kaimori et al. | |
| 2004/0079652 A1 | | 4/2004 | Vreeke et al. | 205/777.5 |
| 2004/0259264 A1 | | 12/2004 | Morita et al. | |
| 2007/0131565 A1 | | 6/2007 | Fujiwara et al. | |

(Continued)

FOREIGN PATENT DOCUMENTS

CN  1394280 A  1/2003
CN  1886651 A  12/2006

(Continued)

OTHER PUBLICATIONS

Extended European Search Report dated Feb. 22, 2011 of the corresponding European patent application (No. 10251688.7).

(Continued)

*Primary Examiner* — Patrick Assouad
*Assistant Examiner* — Christopher McAndrew
(74) *Attorney, Agent, or Firm* — Morgan, Lewis & Bockius LLP (57) ABSTRACT

[Object]
To provide a method for measuring a target component in an erythrocyte-containing specimen with high reliability while suppressing the influence of the Ht value of the specimen.
[Solution to Problem]
In the measurement method of the present invention, first, prior to measurement, a relationship between amounts of the target component and a plurality of signals corresponding thereto is provided. Then, a plurality of signals derived from the target component in the erythrocyte-containing specimen are acquired with a biosensor. With reference to the relationship, the amount of the target component in the specimen is determined based on the thus-acquired plurality of signals.

13 Claims, 3 Drawing Sheets (56) References Cited

U.S. PATENT DOCUMENTS

| | | |
|---|---|---|
| 2007/0138026 A1 | 6/2007 | Fujiwara et al. |
| 2008/0297169 A1* | 12/2008 | Greenquist et al. ........... 324/600 |
| 2009/0152127 A1 | 6/2009 | Kaimori et al. |
| 2009/0184004 A1 | 7/2009 | Chatelier et al. |
| 2010/0206749 A1 | 8/2010 | Choi |
| 2010/0270177 A1 | 10/2010 | Fujiwara et al. |

FOREIGN PATENT DOCUMENTS

| | | | |
|---|---|---|---|
| EP | 1394545 A1 | 3/2004 | |
| EP | 1 645 876 A2 | 4/2006 | |
| EP | 1645876 A2 * | 4/2006 | |
| EP | 2098857 A2 | 9/2009 | |
| JP | 2004-163411 A | 6/2004 | |
| JP | 2006-010706 A | 1/2006 | |
| JP | 2007-303968 A | 11/2007 | |
| JP | 2009-168815 A | 7/2009 | |
| JP | 2009-533658 A | 9/2009 | |
| JP | 2010-507808 A | 3/2010 | |
| KR | 10-2009-0033065 A | 4/2009 | |
| KR | 10-2009-0079821 A | 7/2009 | |
| WO | 99/60391 A1 | 11/1999 | |
| WO | 01/57510 A2 | 8/2001 | |
| WO | 03/036285 A1 | 5/2003 | |
| WO | WO 03/040728 | 5/2003 | |
| WO | 2005/054840 A1 | 6/2005 | |
| WO | 2005/103669 A1 | 11/2005 | |
| WO | 2007/032286 A1 | 3/2007 | |
| WO | 2007/115694 A2 | 10/2007 | |
| WO | WO 2007/121111 A2 | 10/2007 | |
| WO | WO 2008/040998 | 4/2008 | |
| WO | WO 2008040998 A2 * | 4/2008 | |
| WO | 2008/051742 A2 | 5/2008 | |

OTHER PUBLICATIONS

Office Action issued in corresponding Chinese Patent Application No. 201010577012.2 dated Apr. 2, 2013.

* cited by examiner

METHOD FOR MEASURING TARGET COMPONENT IN ERYTHROCYTE-CONTAINING SPECIMEN

This application claims priority to Provisional Application No. 61/247,131, filed Sep. 30, 2009, which is hereby incorporated by reference in its entirety.

TECHNIQUE FIELD

The present invention relates to a method for measuring a target component in an erythrocyte-containing specimen.

BACKGROUND ART

In order to measure a target component in blood, methods of detecting an electrochemical signal or an optical signal with the use of a biosensor have been used widely. A signal value, which indicates the magnitude or intensity of the signal, corresponds to the amount of the target component. Thus, by measuring the signal value, the amount of the target component in blood can be measured.

In such measurement, the influence of the hematocrit value of blood has been regarded as a problem. In general, the normal value of the hematocrit value of blood is set to 30% to 55%. However, the hematocrit value of anemic blood may be lower than the normal value, while the hematocrit value of polysynthetic blood may be higher than the normal value. As such, the Ht value of blood varies from one person to another. Thus, when the measurement of a target component is performed on a blood specimen whose Ht value is unknown, there arises a problem that, owing to the influence of the Ht value, the amount of the target component cannot be determined accurately.

CITATION LIST

Patent Literature

[Patent Literature 1] US2004079652A1
[Patent Literature 2] EP1645876A2
[Patent Literature 3] WO2007121111A2

SUMMARY OF INVENTION

Technical Problem

With the foregoing in mind, it is an object of the present invention to provide a method for measuring a target component in an erythrocyte-containing specimen with high reliability while suppressing the influence of the Ht value of the specimen.

Solution to Problem

The measurement method according to the present invention is a method for measuring a target component in an erythrocyte-containing specimen with a biosensor, including the steps of:

(A) providing a relationship between amounts of the target component and a plurality of signals corresponding thereto prior to measurement;

(B) acquiring a plurality of signals derived from the target component in the erythrocyte-containing specimen with the biosensor; and (C) determining an amount of the target component in the specimen based on the plurality of signals in the step (B) with reference to the relationship in the step (A).

ADVANTAGEOUS EFFECTS OF THE INVENTION

According to the present invention, the influence of the Ht value on the measurement of a target component can be corrected with reference to the relationship between amounts of the target component and a plurality of signals corresponding thereto, thereby allowing the amount of the target component in the erythrocyte-containing specimen to be measured more accurately. Thus, it can be said that the present invention is very useful in the fields of analysis, clinical practice, etc.

The inventors of the present invention found that, in the measurement of the amount of a target component in an erythrocyte-containing specimen based on a signal derived from the target component, (1) even when the amount of the target component is the same, the signal varies depending on the Ht value of the specimen, and (2) when a plurality of signals are measured, the signals vary. Based on these findings, the inventors achieved the present invention by which the amount of a target component in an erythrocyte-containing specimen is measured more accurately with reference to the relationship between amounts of the target component and a plurality of signals corresponding thereto.

DESCRIPTION OF EMBODIMENTS

The measurement method according to the present invention is, as described above, a method for measuring a target component in an erythrocyte-containing specimen with a biosensor, including the steps of:

(A) providing a relationship between amounts of the target component and a plurality of signals corresponding thereto prior to measurement;

(B) acquiring a plurality of signals derived from the target component in the erythrocyte-containing specimen with the biosensor; and (C) determining an amount of the target component in the specimen based on the plurality of signals in the step (B) with reference to the relationship in the step (A).

In the measurement method according to the present invention, "to acquire a signal" also can be referred to as, for example, "to measure a signal". Furthermore, to acquire or measure "a signal" means, for example, to acquire or measure "a signal value", which indicates the magnitude, intensity, or the like of the signal. Still further, variation in signal means, for example, variation in signal value.

In the measurement method according to the present invention, in the step (A), the relationship between amounts of the target component and a plurality of signals corresponding thereto may be provided with regard to different Ht values prior to measurement.

In the measurement method according to the present invention, the plurality of signals may be, for example, signals acquired at a plurality of time points or signals acquired at a plurality of detecting portions. In the following, as the measurement method of the present invention, a first measurement method in which the plurality of signals are signals acquired at a plurality of time points, a second measurement method and a third measurement method in which the plurality of signals are signals acquired at a plurality of detecting portions will be described. It should be noted here that the present invention is not limited to these embodiments.

(First Measurement Method)

The first measurement method according to the present invention is, as described above, a method for measuring a target component in an erythrocyte-containing specimen using, as the plurality of signals, signals acquired at a plurality of time points.

The first measurement method according to the present invention is achieved, as described above, based on the findings of the inventors: (1) even when the amount of the target component is the same, the signal varies depending on the Ht value of the specimen, and (2) when a plurality of signals are measured, the signals vary. The item (1) is the finding that, for example, in the case where the signal is a signal that increases in keeping with the amount of the target component, the signal decreases as the Ht value becomes relatively high and increases as the Ht value becomes relatively low. On the other hand, the item (2) is the finding that, for example, in the case where the signal is a signal that increases in keeping with the amount of the target component, the signal decreases as the time point at which the signal is detected is relatively late in time-course signal detection.

According to the present invention, the Ht value of an erythrocyte-containing specimen, for example, can be converted based on signals acquired at a plurality of time points. Thus, the target component in the specimen can be measured with the influence of the Ht value being corrected. Moreover, according to the present invention, the target component in the specimen can be measured with the influence of the Ht value of the specimen being corrected, for example, without performing the conversion of the Ht value.

In the present invention, it is preferable that, in the step (A), the relationship between amounts of the target component and a plurality of signals corresponding thereto is provided with regard to different Ht values prior to measurement. Furthermore, in the step (A), the above-described relationship may be, for example, the relationship between a plurality of signals corresponding to amounts of the target component and Ht values.

The signals acquired at a plurality of time points means, for example, signals acquired more than once over time. The number of the time points, i.e., the number of times that the signal acquisition is performed is not particularly limited as long as it is plural. For example, it is two or more, preferably two to four, more preferably two to three, and still more preferably two.

The plurality of signals preferably are, for example, signals acquired at the same detecting portion.

The time interval at which the signals are acquired is not particularly limited, and can be determined as appropriate depending on, for instance, the kind of the signals, the kind of the target component, conditions for generating the signals, etc. As a specific example, it is preferable that the plurality of signals are, for example, signals acquired at a time interval of 1 to 20 seconds, more preferably 5 to 10 seconds, and still more preferably 4 to 5 seconds.

With regard to the plurality of signals, the start time and termination time for signal acquisition are not particularly limited, and can be determined as appropriate depending on, for instance, the kind of the signals, the kind of the target component, conditions for generating the signals, etc. Among the plurality of signals, the signal acquired first preferably is, for example, a signal that is generated between second 1 and second 20 inclusive, more preferably between second 5 and second 10 inclusive, and still more preferably between second 4 and second 5 inclusive, assuming that the time point at which signal generation becomes possible is second 0. Furthermore, among the plurality of signals, the signal acquired last preferably is, for example, a signal that is generated between second 5 and second 20 inclusive, more preferably between second 5 and second 10 inclusive, and still more preferably between second 5 and second 6 inclusive, assuming that the time point at which signal generation becomes possible is second 0.

In the first measurement method of the present invention, the timing of acquiring the signals is not particularly limited, and can be determined as appropriate depending on, for example, the kind of the signals, the kind of the target component, conditions for generating the signals, etc. Specific examples are as follows. The plurality of signals preferably are, for example, signal generated on or after second 10, more preferably on or after second 6, and still more preferably on or after second 4, assuming that the time point at which signal generation becomes possible is second 0. Furthermore, the plurality of signals preferably are, for example, signal generated up until second 20, more preferably up until second 10, and still more preferably up until second 5, assuming that the time point at which signal generation becomes possible is second 0. Still further, the signals preferably are, for example, signals generated between second 10 and second 15 inclusive, more preferably between second 6 and second 10 inclusive, and still more preferably between second 4 and second 5 inclusive, assuming that the time point at which signal generation becomes possible is second 0.

In the first measurement method of the present invention, the signal can be, for example, a signal that can be detected by electrochemical measurement (hereinafter, such a signal is also referred to as an "electrical signal"). In this case, it is preferable that the electrical signal is, for example, a signal that can be detected by a working electrode as a detecting portion of the biosensor.

The kind of the electrical signal is not particularly limited, and can be, for example, a current, a voltage converted from a current, and digital signals corresponding thereto. Interconversion of these electrical signals is possible by, for instance, known methods. As a specific example, when a current is measured by the electrochemical measurement, the current can be converted to a voltage with, for example, a current/voltage transducer or the like, and a voltage, which is an analog signal, can be converted to a digital signal with, for example, an A/D (analog/digital) transducer.

The time interval at which the electrical signals are acquired is not particularly limited, and can be determined as appropriate depending on, for instance, the kind of the target component, conditions for generating the electrical signals, etc. As a specific example, it is preferable that the plurality of electrical signals are, for example, electrical signals acquired at a time interval of 1 to 10 seconds, more preferably 1 to 5 seconds, and still more preferably 1 to 2 seconds.

With regard to the plurality of electrical signals, the start time and termination time for acquisition thereof are not particularly limited, and can be determined as appropriate depending on, for instance, the kind of the target component, conditions for generating the electrical signals, etc. Among the plurality of electrical signals, the electrical signal acquired first preferably is, for example, a signal that is generated between second 1 and second 20 inclusive, more preferably between second 5 and second 10 inclusive, and still more preferably between second 4 and second 5 inclusive, assuming that the time of voltage application is second 0. Furthermore, among the plurality of electrical signals, the electrical signal acquired last preferably is, for example, a signal that is generated between second 5 and second 20 inclusive, more preferably between second 5 and second 10 inclusive, and still more preferably between second 5 and second 6 inclusive, assuming that the time of voltage application is second 0.

The timing of acquiring the electrical signals is not particularly limited, and can be determined as appropriate depending on, for example, the kind of the target component, conditions for generating the electrical signals, etc. Specific examples are as follows. The plurality of electrical signals preferably are, for example, signal generated on or after second 10, more preferably on or after second 5, and still more preferably on or after second 4, assuming that the time of voltage application is second 0. Furthermore, the plurality of electrical signals preferably are, for example, signal generated up until second 20, more preferably up until second 10, and still more preferably up until second 5, assuming that the time of voltage application is second 0. Still further, the plurality of electrical signals preferably are, for example, signals generated between second 1 and second 20 inclusive, more preferably between second 5 and second 10 inclusive, and still more preferably between second 4 and second 5 inclusive, assuming that the time of voltage application is second 0.

Furthermore, in the first measurement method of the present invention, the signal can be, for example, a signal that can be detected by optical measurement (hereinafter, such a signal is also referred to as an "optical signal"). The kind of the optical signal is not particularly limited, and examples thereof include an absorbance, a reflectance, a transmittance, and digital signals corresponding thereto. Interconversion of these optical signals is possible by, for instance, known methods.

The optical signal can be detected by a detector, for example. The detector may be disposed, for example, in the biosensor or outside the biosensor. In the latter case, for example, the biosensor may previously be connected to the detector before the detection of the optical signal, or the biosensor may be connected to the detector when carrying out the detection.

The time interval at which the optical signals are acquired is not particularly limited, and can be determined as appropriate depending on, for instance, the kind of the target component, conditions for generating the optical signals, etc. As a specific example, it is preferable that the plurality of optical signals are, for example, optical signals acquired at a time interval of 1 to 20 seconds, more preferably 5 to 10 seconds, and still more preferably 4 to 5 seconds.

With regard to the plurality of optical signals, the start time and termination time for acquisition thereof are not particularly limited, and can be determined as appropriate depending on, for instance, the kind of the target component, conditions for generating the optical signals, etc. Among the plurality of optical signals, the optical signal acquired first preferably is, for example, a signal that is generated between second 1 and second 20 inclusive, more preferably between second 5 and second 10 inclusive, and still more preferably between second 4 and second 5 inclusive, assuming that the time point at which signal generation becomes possible is second 0. Furthermore, among the plurality of optical signals, the optical signal acquired last preferably is, for example, a signal that is generated between second 5 and second 20 inclusive, more preferably between second 5 and second 10 inclusive, and still more preferably between second 5 and second 6 inclusive, assuming that the time point at which signal generation becomes possible is second 0. The time point at which signal generation becomes possible can be, for example, the time point at which a reaction for generating the optical signals is started.

The timing of acquiring the optical signals is not particularly limited, and can be determined as appropriate depending on, for example, the kind of the target component, conditions for generating the optical signals, etc. Specific examples are as follows. The plurality of optical signals preferably are, for example, signal generated on or after second 10, more preferably on or after second 6, and still more preferably on or after second 4, assuming that the time point at which signal generation becomes possible is second 0. Furthermore, the plurality of optical signals preferably are, for example, signal generated up until second 20, more preferably up until second 10, and still more preferably up until second 5, assuming that the time point at which signal generation becomes possible is second 0. Still further, the plurality of optical signals preferably are, for example, signals generated between second 1 and second 20 inclusive, more preferably between second 5 and second 10 inclusive, and still more preferably between second 4 and second 5 inclusive, assuming that the time point at which signal generation becomes possible is second 0.

In the first measurement method of the present invention, the signal can be, for example, a signal based on a redox reaction with the target component. The kind of the redox reaction can be determined as appropriate depending on, for example, the kind of the target component.

The redox reaction is not particularly limited, and can be, for example, a redox reaction using a necessary reagent depending on the kind of the target component. Specific examples of the redox reaction include a reaction using an enzyme that catalyzes at least one of an oxidation reaction and a reduction reaction and a mediator or a color-developing substrate. When the signal is an electrical signal, an electron transfer substance, for example, can be used as the mediator. Specific examples of the electron transfer substance include ruthenium complexes, iron complexes, other organometalic complexes, organometallic complex polymers, conducting ionic salts, and organic mediator compounds such as benzoquinone. The enzyme can be determined as appropriate depending on, for example, the kind of the target component, and examples thereof include oxidation enzymes, reduction enzymes, and oxidoreductases. When the signal is an optical signal, the color-developing substrate can be a color-developing substrate that develops color by oxidation or reduction, a fluorescence substrate that emits fluorescence by oxidation or reduction, or the like. The enzyme and also the mediator or the color-developing substrate preferably are immobilized on, for example, a portion to which a specimen is supplied, a portion where a specimen moves, or the like of a biosensor.

In the first measurement method of the present invention, the step (A) is, as described above, a step of providing a relationship between amounts of the target component and a plurality of signals corresponding thereto (hereinafter, also referred to as a "specific relationship"). With reference to this specific relationship, influence of the Ht value on the measurement of the target component can be corrected, whereby the amount of the target component in the erythrocyte-containing specimen can be measured more accurately. The method for setting this specific relationship is not particularly limited. For example, the specific relationship can be set by acquiring a plurality of signals with regard to standard specimens with known target component concentrations. Furthermore, it is preferable that the standard specimens with known target component concentrations are derived from each of a plurality of standard specimens with different Ht values.

The plurality of signals with regard to the standard specimen are not particularly limited, and can be acquired, for instance, in the following manner.

First, a plurality of standard specimens with different Ht values are provided. The number of the kinds of the standard specimens are not particularly limited, and can be, for example, two or more, preferably three or more, more preferably 5 or more, and particularly preferably 10 or more. For example, since more reliable measurement becomes possible as the number of the kinds of the standard specimens is relatively large, the upper limit of the number of the kinds is not particularly limited. The Ht values of the standard specimens are not particularly limited. The Ht values of the standard specimens need only to be, for example, different Ht values as described above, and the different Ht values may be either known or unknown. The Ht values of the standard specimens preferably are within the range including a normal value and an abnormal value, for example. In general, the normal value of the Ht value is about 30% to 55%, the upper limit of the abnormal value is about 70%, and the lower limit of the same is about 10%. Therefore, the Ht values of the standard specimens preferably are, for example, within the range of 10% to 70%. It is preferable that the plurality of standard specimens include at least, in particular, a standard specimen whose Ht value is in the vicinity of the upper limit, a standard specimen whose Ht value is in the vicinity of the lower limit, and a standard specimen whose Ht value is a normal value.

Next, the target component concentration in each of the standard specimens is varied, thereby providing a target component concentration series for each standard specimen. The target component concentrations may vary, for example, from one standard specimen to another, but it is preferable that all the standard specimens have the same target component concentration. The number of the kinds of the target component concentrations included in the concentration series of the standard specimen, i.e., the variations of the target component concentration, is not particularly limited, and can be, for example, two or more, preferably three or more, more preferably 5 or more, and particularly preferably 10 or more. As the number of the kinds of the target component concentrations included in the concentration series is relatively large, more reliable measurement becomes possible. Thus, for example, the upper limit of the kinds is not limited. The concentrations included in the target component concentration series are not particularly limited, and can be determined as appropriate depending on, for example, the kind of the target component, conditions for generating the signals, the method for acquiring the signals, etc. It is preferable to set the concentrations within the range including a normal value and an abnormal value depending on, for example, the kind of the target component. Within this range, the concentrations preferably include at least a concentration in the vicinity of the upper limit, a concentration in the vicinity of the lower limit, and a concentration that is a normal value. This will be explained by taking glucose as an example of the target component. The normal value of the glucose generally is about 80 to 180 mg/dL, the upper limit of the glucose is about 600 mg/dL, and the lower limit of the glucose is about 20 mg/dL. Therefore, the glucose concentration series preferably is set so as to be fall within the range, for example, from 20 to 600 mg/dL. It is to be noted that glucose is given merely as an example, and the target component in the present invention is by no means limited thereto.

Then, with regard to the target component concentration series of each standard specimen, a plurality of signals are acquired. It is preferable that the acquisition of the plurality of signals is carried out under the same conditions and by the same method for all the standard specimens. It is also preferable that the acquisition of the plurality of signals is carried out under the same conditions and by the same method as those for the signal acquisition from the erythrocyte-containing specimen in the step (B) that will be described later.

From the plurality of signals thus obtained and the target component concentrations in the standard specimens, it is possible to derive the relationship between amounts of the target component and a plurality of signals corresponding thereto. This specific relationship represents the signal variation caused by the Ht value, signal variation caused when signals are measured at a plurality of time points (variation in signal value over time), and variations of the signals corresponding to the amounts of the target component. Thus, based on the relationship, it is possible to determine, for example, the concentration of the target component considering the influence of the Ht value from the plurality of signals measured for the erythrocyte-containing specimen.

In the first measurement method of the present invention, the way of expressing the specific relationship is by no means limited, and for example, a calibration curve, a calibration table, a regression equation, etc. can be applied.

The following description is directed to an example where the specific relationship is expressed as a regression equation. As the regression equation, a regression equation set in the following step (X) can be used, for example. That is, in the first measurement method of the present invention, it is preferable that the relationship between amounts of the target component and a plurality of signals corresponding thereto with regard to different Ht values in the step (A) is a regression equation determined by the following step (X).

The step (X) is the step of:

acquiring a plurality of signals with regard to a target component concentration series of each of standard specimens having different Ht values, determining a correlation equation between the plurality of signals with regard to each of the standard specimens, selecting any one of the standard specimens as a reference specimen showing a reference Ht value, setting the correlation equation of the selected reference specimen as a reference correlation equation, and determining a regression equation for converging the correlation equations of the respective standard specimens to the reference correlation equation.

It is to be noted here that, in the present invention, using the regression equation determined by the above step (X) is one example, and even in the case where the regression equation is used, the step (X) is not essential in the present invention.

Although an illustrative example of the step (X) will be described in the following, it is to be noted that the present invention is not limited thereto. In the step (X), first, a plurality of signals are acquired for a target component concentration series of each of standard specimens having different Ht values in the same manner as described above. Then, based on the thus-obtained plurality of signals, a correlation equation between the plurality of signals is determined with regard to each standard specimen. The correlation equation can be determined by a conventionally known technique. For example, common computational software can be used.

On the other hand, any one of the standard specimens is selected as a reference specimen showing a reference Ht value. The selection of the reference specimen can be made arbitrarily, and there is no particular limitation thereon. For example, among the standard specimens, the standard specimen showing an intermediate Ht value, the standard specimen showing a normal Ht value, or the like can be selected.

Then, the correlation equation of this reference specimen is set as a reference correlation equation, and a regression equation for converging the correlation equations of the respective standard specimens to the correlation equation of the reference specimen is determined. This regression equation is referred to as the specific relationship in the step (C) that will be performed later. The regression equation can be determined by a conventionally known technique. For example, common computational software can be used.

The specific relationship is not limited to, for example, the regression equation, and can be expressed as a calibration curve, a calibration table, or the like, for example. They also can be prepared by acquiring a plurality of signals with regard to a target component concentration series of a plurality of standard specimens, similarly to the case of the regression equation, for example.

In the measurement method of the present invention, the step (B) is, as described above, a step of acquiring a plurality of signals derived from the target component in the erythrocyte-containing specimen. The signal acquisition from the erythrocyte-containing specimen preferably is carried out, for example, under the same condition and by the same method as those for the above-described signal acquisition from the standard specimen.

In the measurement method of the present invention, the step (C) is, as described above, a step of determining an amount of the target component in the specimen based on the plurality of signals in the step (B) with reference to the specific relationship in the step (A). The specific relationship indicates, as described above, the relationship between amounts of the target component and a plurality of signals corresponding thereto.

By referring to the specific relationship, the amount of the target component considering the Ht value of the erythrocyte-containing specimen can be determined, for example, in the following manner. This specific relationship represents, as described above, signal variation caused by the Ht value, signal variation caused when signals are measured at a plurality of time points (signal variation over time), and variations of the signals corresponding to the amounts of the target component. Thus, by referring to the specific relationship, even in the case where, for example, the Ht value of the erythrocyte-containing specimen is unknown, it becomes possible to determine the amount of the target component from a plurality of signals measured from the specimen with consideration given to the signal variation caused by the Ht value.

Furthermore, in the step (C), the regression equation exemplified in the step (A) can be referred to as the specific relationship, for example. The regression equation is, as described above, a regression equation for converging the correlation equations of the respective standard specimens to the correlation equation of the reference specimen (the reference correlation equation). In this case, the amount of the target component in the erythrocyte-containing specimen can be determined in the following manner, for example. That is, for example, even in the case where the plurality of signals measured from the specimen do not fit the reference correlation equation, the plurality of signals can be corrected to the signals that fit the correlation equation of the reference specimen based on the regression equation. In other words, the signals can be corrected considering the signal variation caused by the Ht value. Hence, by assuming that the plurality of corrected signals are a plurality of signals of the reference specimen, the amount of the target component can be determined with reference to the relationship between a plurality of signals of the reference specimen and amounts of the target component.

Furthermore, in the step (C), a calibration equation described below also can be used. That is, the first measurement method of the present invention can be carried out by, in the step (C), referring to the relationship in the step (A), determining a plurality of corrected signals from the plurality of signals in the step (B), and then determining the amount of the target component in the specimen from the plurality of corrected signals with reference to a calibration equation determined by the following step (Y).

The step (Y) is the step of:

acquiring a plurality of signals with regard to the target component concentration series of the reference specimen showing the reference Ht value, and determining, as the calibration equation, a correlation equation between the plurality of signals and amounts of the target component in the reference specimen.

It is to be noted here that, in the present invention, using the calibration equation determined by the following step (Y) is one example, and the step (Y) is not essential in the present invention.

According to the first measurement method of the present invention, it is possible to suppress the influence of the Ht value, which indicates the amount of erythrocytes, on the measurement. Thus, as described above, the first measurement method is applied to an erythrocyte-containing specimen. Examples of the erythrocyte-containing specimen include a whole blood specimen. The whole blood specimen can be, for example, untreated whole blood, diluted whole blood, or hemolyzed whole blood.

In the measurement method of the present invention, the target component is by no means limited, and can be any component contained or considered to be contained in an erythrocyte-containing specimen. Examples of the component include sugars such as glucose, C-reactive protein (CRP), HbA1c, thyroid-stimulating hormone (TSH), FT3, FT4, hCG, HBs antigen, HBc antibody, HCV antibody, TY antigen, antistreptolysin O (ASO), type IV collagen, matrix metalloproteinase (MMP-3), PIVAK-II, α1 microglobulin, β1 microglobulin, amyloid A (SAA), elastase 1, basic fetoprotein (BFP), candida antigen, granulocyte elastase in cervical mucus, digoxin, cystatin C, factor XIII, urinary transferring, syphilis, hyaluronic acid, fibrin monomer complex (SFMC), von Willbrand factor (factor VIII antigen), protein S, rheumatoid factor (RF), IgD, a1 acid glycoprotein (α1AG), α1 antitrypsin (α1AT), α2 macroglobulin, albumin (Alb), ceruloplasmin (Cp), haptoglobin (Hp), prealbumin, retinol-binding protein (RBP), β1C/β1A globulin (C3), β1E globulin (C4), IgA, IgG, IgM, β lipoprotein (β-LP), apoprotein A-I, apoprotein A-II, apoprotein B, apoprotein C-II, apoprotein apoprotein E, transferring (Tf), urinary albumin, plasminogen (PLG), lipoprotein (a) (LP (a)), lactate, low density lipid, high density lipid and triglyceride, and the like.

In the first measurement method of the present invention, the biosensor to be used is not particularly limited, and any conventional biosensor can be used. The kind of the biosensor is not particularly limited, and can be selected as appropriate depending on, for example, the kind of the signals, i.e., whether the signals are electrical signals or optical signals, etc. Hereinafter, the biosensor used in an electrochemical measurement method is referred to as an electrical biosensor, and the biosensor used in an optical measurement method is referred to as an optical biosensor.

In the first measurement method of the present invention, signal measurement can be achieved by measuring signals at a plurality of time points. Thus, it is only necessary that the biosensor include, for example at least one detecting portion.

When the signals are electrical signals, it is preferable to use an electrical biosensor including a working electrode as a detecting portion. In the electrical biosensor, the number of working electrodes is not particularly limited, and the electrical biosensor may include at least one working electrode. Specifically, it is preferable that the electrical biosensor is provided with at least one set of electrode group including a working electrode and a counter electrode. At the time of signal detection, a signal such as a current can be measured from the working electrode by applying a voltage between the working electrode and the counter electrode of the electrical biosensor. Furthermore, the biosensor may have a plurality of working electrodes, and the number of the working electrodes is, for instance, two or more, preferably two, In this case, signals may be acquired at a plurality of time points in each of the working electrodes. The plurality of working electrodes may be, for example, different working electrodes. Examples of the different working electrodes include those made of different materials and those coated with different reagents for detecting the target component.

By using the electrical biosensor, the signal can be detected by, for example, a detector connected to the working electrode. The detector may be disposed, for example, in the biosensor or outside the biosensor. In the latter case, for example, the biosensor may previously be connected to the detector before the detection of the optical signals, or the biosensor may be connected to the detector when carrying out the detection.

To the working electrode, the detector may be connected via a terminal, for example. The detector is not particularly limited, and can be, for example, a current detector, which may include a current/voltage transducer, an A/D transducer, a computing unit, etc.

In the electrical biosensor, it is preferable that a reagent is disposed in, for example, a region to which a specimen is added or a region where a specimen moves, as necessary. The reagent can be determined as appropriate depending on, for example, the kind of the target component, the kind of the redox reaction for generating the signals, etc. Examples of the reagent include the above-described mediators and enzymes.

When the signals are optical signals, an optical biosensor can be used, for example. In the optical biosensor, the detecting portion can be, for example, a reaction region where a specimen reacts with a reagent. In the present invention, for example, a reaction of the specimen with the reagent may be started in the reaction region, or a reaction solution containing the specimen and the reagent may be introduced into the reaction region. In the former case, for example, the reagent may previously be disposed in the reaction region, or the reagent disposed in a different region may be introduced into the reaction region before being mixed with the specimen. In the latter case, for example, the reagent may be disposed in a region different from the reaction region, and after the reagent is mixed with the specimen, the reaction solution may be introduced into the reaction region.

(Second Measurement Method)

The second measurement method according to the present invention is, as described above, a method for measuring a target component in an erythrocyte-containing specimen using, as the plurality of signals, signals acquired at a plurality of detecting portions. Note here that unless otherwise stated, the second measurement method of the present invention can be carried out in the same manner as the first measurement method of the present invention.

The number of the detecting portions is not particularly limited, and can be, for example, two or more, preferably two to 5, more preferably 2 to 3, and still more preferably two.

In the second measurement method of the present invention, the biosensor to be used is not particularly limited as long as it includes a plurality of detecting portions as described above, and any conventional biosensor can be used.

When the signals are electrical signals, for example, it is preferable to use an electrical biosensor having a plurality of working electrodes. Preferably, the electrical signals are measured from the respective working electrodes. The number of the working electrodes is, for example, two or more, preferably two to 5, more preferably 2 to 3, and still more preferably two. Specifically, the electrical biosensor preferably has, for example, a plurality of electrode groups, each including a working electrode and a counter electrode. That is, the electrical biosensor preferably has two or more sets of electrode groups, more preferably two to 5 sets of electrode groups, more preferably 2 to 3 sets of electrode groups, and still more preferably two sets of electrode groups. The number of the counter electrodes in the biosensor is by no means limited. It may be one or also may be two or more. For example, the respective electrode groups may have different counter electrodes, or a counter electrode in one electrode group may also serves as a counter electrode of another electrode group.

When the biosensor has a plurality of working electrodes, it is preferable that the working electrodes are, for example, different working electrodes. Specifically, it is preferable that the plurality of working electrodes are electrodes that exhibit different chemical reactions with the target component. In this case, in the respective electrodes, the respective chemical reactions are influenced by the hematocrit. Thus, by providing the relationships between amounts of the target component and signals corresponding thereto acquired at the respective electrodes as, the specific relationship, it becomes possible to correct the influence of the hematocrit. Signal measurements at the respective electrodes preferably are performed at the same time, for example. Examples of the electrodes exhibiting different chemical reactions include those made of different materials and those coated with different reagents for detecting the target component.

On the other hand, when the signals are optical signals, an optical biosensor having a plurality of detecting portions can be used, for example. In the optical biosensor, the detecting portion can be, for example, a reaction region where a specimen reacts with a reagent.

(Third Measurement Method)

The third measurement method according to the present invention is a method for measuring a target component in an erythrocyte-containing specimen using signals acquired at a plurality of detecting portions. The detecting portions are arranged, for example, so as to be in parallel with a specimen moving direction and located at different distances from the portion to which a specimen is added.

The third measurement method according to the present invention is achieved, as described above, based on the findings of the inventors: (1) even when the amount of the target component is the same, the signal varies depending on the Ht value of the specimen; and (2) when a plurality of signals are measured, the signals vary. The item (1) is, as described above, the finding that, for example, in the case where the signal is a signal that increases in keeping with the amount of the target component, the signal decreases as the Ht value becomes relatively high and increases as the Ht value becomes relatively low. On the other hand, the item (2) is the finding that, for example, in the case where the signal is a signal that increases in keeping with the amount of the target component, the signal decreases as it is detected at a detecting portion relatively further from a portion to which a specimen is added. Presumably, the reason for this is that the diffusion speed of the specimen is reduced depending on the Ht value and the influence thereof is reflected in the signal values. Specifically, it is presumed that the signal decreases, for example, because the diffusion speed of the specimen becomes relatively slow as the Ht value becomes relatively high.

As long as the specific relationship is referred to, the present invention is not limited to the embodiments shown for illustrative purpose.

Hereinafter, the present invention will be described more specifically by way of examples. It is to be noted, however, the present invention is by no means limited to these examples.

EXAMPLES

Example 1

Using venous blood, standard specimens having predetermined Ht values (29%, 41%, and 55% (±2%)) were prepared (hereinafter, these specimens are referred to as Ht 29%, Ht 41%, and Ht 55%). Then, for each of these standard specimens, samples of a glucose concentration series were prepare so that they had predetermined glucose concentrations (50, 100, 150, 250, 350, and 550 mg/dL).

Modified Advance meters (trade name, manufactured by Hypoguard, meters with modified software to allow current transient collection) as current measurement devices and 2 pots of Menarini Glucomen GM strips (trade name, manufactured by Arkray) as biosensors, current measurement was carried out in accordance with their instructions. The current measurement was performed at second 5 and second 10, assuming that the time of voltage application was second 0. The measurement was carried out eight times per each sample, and the average value of the thus-obtained measured values was determined.

Figure 1:
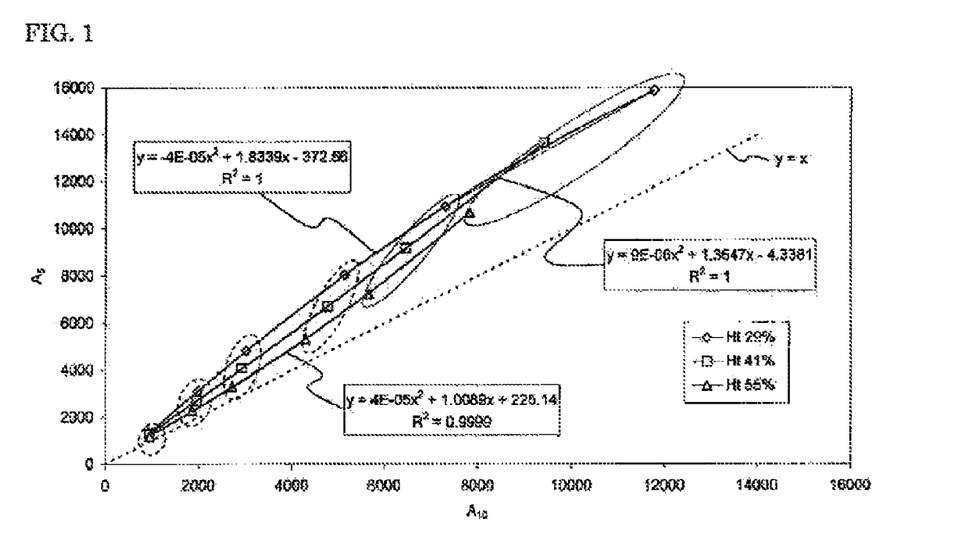
FIG. 1 is a graph showing the relationship between currents measured after 5 seconds and 10 seconds from the voltage application with regard to standard specimens containing glucose and showing predetermined Ht values in Example 1 of the present invention.

The results of the measurement are shown in FIG. 1. FIG. 1 is a graph plotting a current ($A_5$) measured after 5 seconds from the voltage application (hereinafter referred to as a "second-5 current ($A_5$)") and the current ($A_{10}$) measured after 10 seconds from the voltage application (hereinafter referred to as a "second-10 current ($A_{10}$)") with regard to the glucose concentration series of each standard specimen. In FIG. 1, the X axis indicates the second-10 current ($A_{10}$), while the Y axis indicates the second-5 current ($A_5$). Furthermore, in FIG. 1, a open diamond (◇) shows the result of the Ht 29%, a open square (□) shows the result of the Ht 41%, and a open triangle (Δ) shows the result of the Ht 55%. Still further, in FIG. 1, each three plots that are encircled indicate, from the left, the result when the glucose was 50 mg/dL, the result when the glucose was 100 mg/dL, the result when the glucose was 150 mg/dL, the result when the glucose was 250 mg/dL, the result when the glucose was 350 mg/dL, and the result when the glucose was 550 mg/dL. The current plotted is an average value.

As a result of the above-described two time-point current measurement for each sample, the following facts were revealed. First, the current value of the Ht 55% was the lowest while the current value of the Ht 29% was the highest for all the glucose concentrations. This indicates that the current value behaves such that, under the influence of the Ht value, it decreases with the increase in the Ht value and increases with the decrease in the Ht value. Furthermore, as a result of the two time-point current measurement, the second-10 currents ($A_{10}$) were lower than the second-5 currents ($A_5$). This indicates that the current value behaves such that, under the influence of the Ht value, it decreases as the time elapsed from the voltage application until the current value is measured becomes longer. FIG. 1 is the graph showing these behaviors. Therefore, it can be said that, based on these behaviors, the influence of the Ht value can be corrected from the results of the two time-point current measurement.

Figure 2:
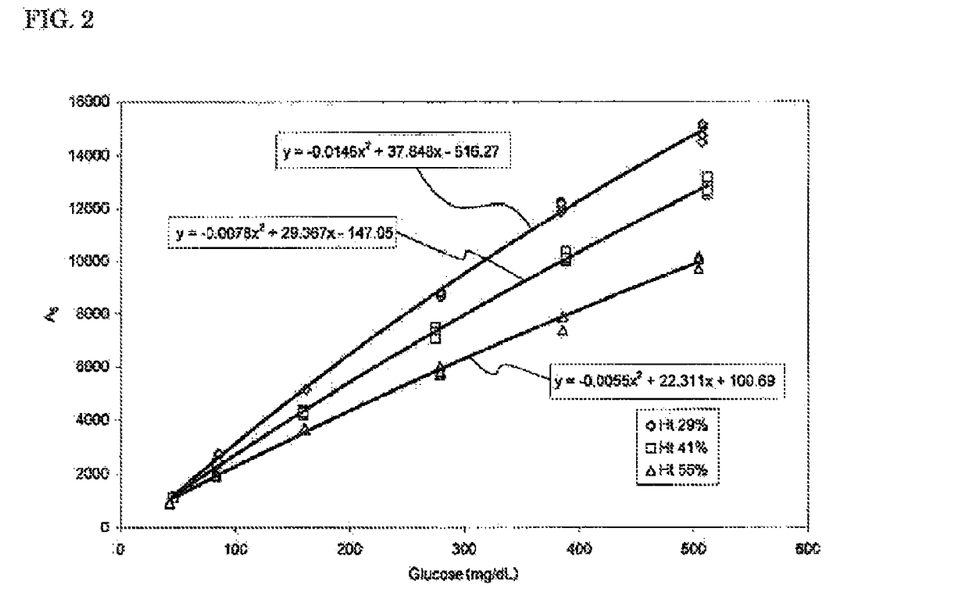
FIG. 2 is a graph showing the relationship between currents measured after 5 seconds from the voltage application and glucose concentrations with regard to standard specimens containing glucose and showing predetermined Ht values.

On the other hand, FIG. 2 shows a graph plotting the glucose concentration and the second-5 current ($A_5$) with regard to the glucose concentration series of each standard specimen. In FIG. 2, a open diamond (◇) shows the second-5 current ($A_5$) with regard to the Ht 29%, a open square (□) shows the second-5 current ($A_5$) with regard to the Ht 41%, and a open triangle (Δ) shows the second-5 current ($A_5$) with regard to the Ht 55%. In. FIG. 2, the current plotted is an average value.

In the case where only currents measured at one time point are plotted as shown in FIG. 2, assuming that the measured current was 8000 nA, for example, the plot of 8000 nA is presence for each standard specimen. Thus, as long as the Ht value of the specimen is unknown, the following three glucose concentrations are derived: about 250 mg/dL based on the result of the Ht 29% (◇); about 300 mg/dL based on the result of the Ht 41% (□); and about 390 mg/dL based on the result of Ht 55% (Δ). Thus, the Ht value cannot be corrected, so that the measurement result lucks accuracy Example 2

Subsequently, from the results shown in FIG. 1, a quadratic polynomial expressing the correlation between a second-5 current ($A_5$) and a second-10 current ($A_{10}$) was determined for each standard specimen. The results are shown below. In the following equations, y is a second-5 current ($A_5$) and x is a second-10 current ($A_{10}$).

*Ht* value 29%; $y=-4E-05x^2+1.8339x-372.56$ $R^2=1$

*Ht* value 41%: $y=9E-06x^2+1.3647x-4.3381$ $R^2=1$

*Ht* value 55%: $y=4E-05x^2+1.0089x+225.14$ $R^2=0.9999$

Figure 3:
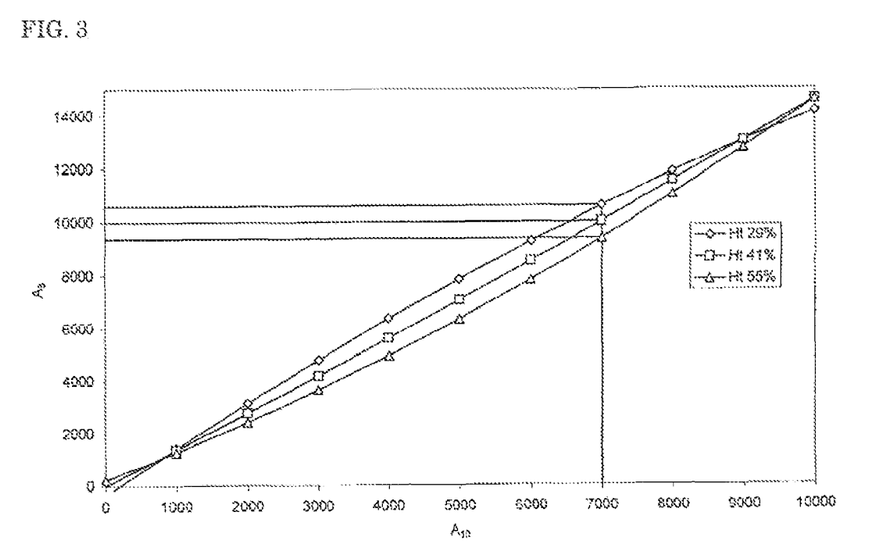
FIG. 3 is a graph plotting the relationship between second-10 currents ($A_{10}$) and second-5 currents ($A_5$) based on quadratic polynomials in Example 2 of the present invention.

Then, into "x" in each of these quadratic polynomials, the second-10 currents ($A_{10}$) from 0 to 12000 nA shown in the following table were substituted, whereby the corresponding second-5 currents ($A_5$) were calculated. These results also are shown in the following table and FIG. 3. With reference to Table 1 as a look-up table or FIG. 3 as a look-up drawing, it is possible to convert the hematocrit regardless of whether the measured current is a second-5 current ($A_5$) or a second-10 current ($A_{10}$).

TABLE 1

| $A_{10}$ (nA) | $A_5$ (nA) | | |
| --- | --- | --- | --- |
| | Ht 29% | Ht 41% | Ht 55% |
| 0 | −373 | −4 | 225 |
| 1000 | 1423 | 1369 | 1276 |
| 2000 | 3141 | 2762 | 2412 |
| 3000 | 4782 | 4172 | 3632 |
| 4000 | 6346 | 5600 | 4937 |
| 5000 | 7833 | 7047 | 6326 |
| 6000 | 9243 | 8512 | 7799 |
| 7000 | 10576 | 9996 | 9357 |
| 8000 | 11832 | 11497 | 11000 |
| 9000 | 13011 | 13017 | 12727 |
| 10000 | 14113 | 14556 | 14538 |
| 11000 | 15137 | 16112 | 16434 |
| 12000 | 16085 | 17687 | 18415 |

Figure 4:
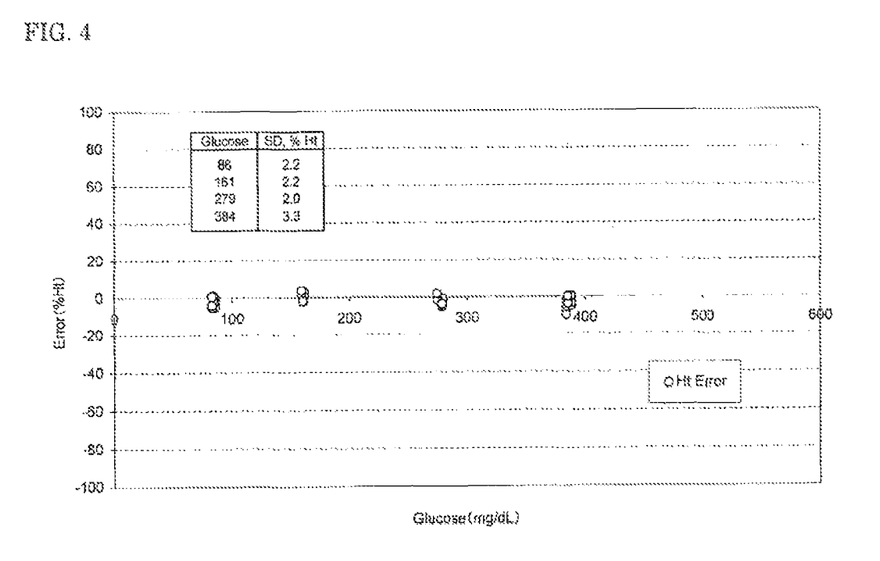
FIG. 4 is a graph showing errors (% Ht) in Ht value corrected by an algorithm in Example 2 of the present invention.

Then, based on Table 1 above, the Ht error, i.e., the difference between the calculated Ht value and the actual Ht value was determined. Specifically, specimens having known Ht values and predetermined glucose concentrations (86 mg/dL, 161 mg/dL, 279 mg/dL and 386 mg/dL) were provided. With regard to each specimen, a current at second 10 was measured, and the Ht value of the specimen was calculated based on Table 1. Then, with regard to the thus-calculated Ht value, the difference from the known Ht value was determined. The results are shown in FIG. 4. FIG. 4 is a graph showing Ht errors (% Ht) with regard to the respective glucose specimens. As shown in FIG. 4, the specimens whose glucose concentrations were in the range from about 80 mg/dL to about 400 mg/dL exhibited very low Ht error values. Thus, based on Table 1 and FIG. 3, the hematocrit can be converted more accurately when the glucose concentration is within the above-described range.

Example 3

Using the measurement results obtained in Example 1, an algorithm for converging the current values measured for the respective glucose concentrations with regard to the Ht 55% and the current values measured for the respective glucose concentrations with regard to the Ht 29% to the current values measured for the corresponding glucose concentrations with regard to the Ht 41% was determined using a commercially available program Microsoft Office Excel. This algorithm is shown below.

1. A $2^{nd}$ order quadratic polynomial is created based upon the mid point Ht (41%) glucose response against the second-10 current ($A_{10}$). Two columns can be used here, glucose and current. This is the uncorrected glucose polynomial.
2. From [1] calculate the glucose based on the current measured at second 10. This is the uncorrected glucose value.
3. From the Ht-current table (Table 1) interpolate a Ht value using the currents measured at second 5 and second 10. This is the Ht estimate.
4. Using $2^{nd}$ degree quadratic polynomials fitted to the low (29%) Ht, mid Ht(41%) and high (55%) Ht on the glucose and uncorrected glucose values [see 2], calculate a glucose value based upon a uncorrected glucose value of 200 mg/dL, this will give a glucose value carrying the Ht induced error, for the 29% Ht, 41% Ht, and 55% Ht the Ht error glucose $_{200}$ values (the mid 41% Ht value will be 200 mg/dL as this carries no error).
5. Using the glucose 200 values calculated for the three Ht from [4] calculate a $2^{nd}$ order quadratic polynomial of Ht against Ht error glucose $_{200}$. This is the Ht correction polynomial.
6. Using the uncorrected glucose value, the Ht estimate and the Ht correction polynomial calculate a corrected glucose estimate based upon a Ht of 41%. This is the final corrected glucose estimate.

Figure 5:
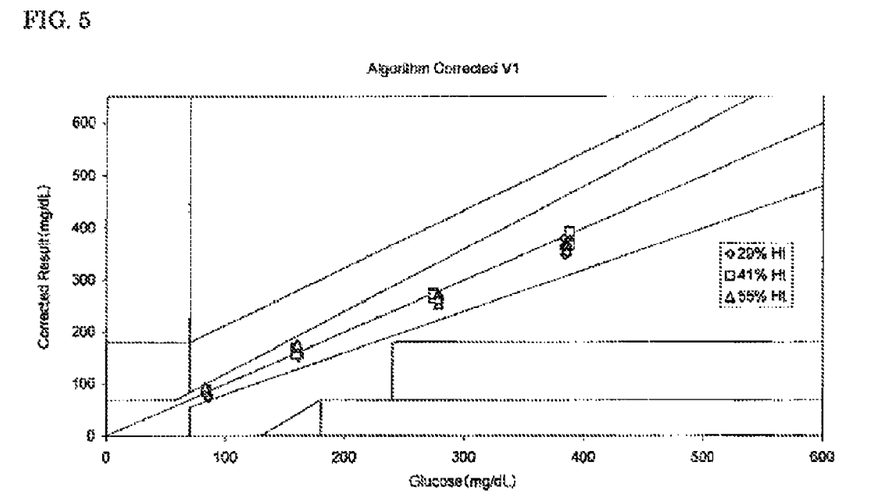
FIG. 5 is a graph showing the relationship between glucose concentrations corrected by an algorithm and known glucose concentrations in Example 4 of the present invention.
Figure 6:
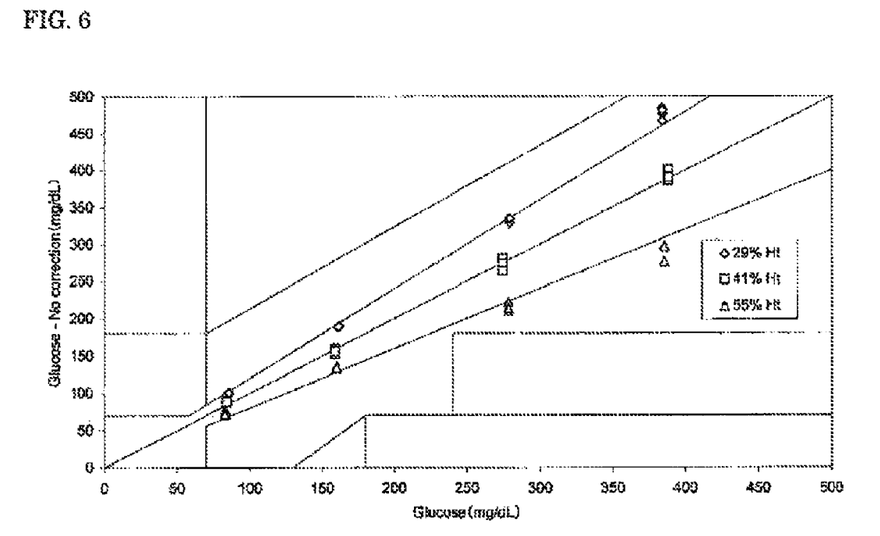
FIG. 6 is a graph showing the relationship between glucose concentrations estimated by a conventional algorithm and known glucose concentrations.

Then, from the current values measured at the two time points for the respective standard specimens in Example 1, the glucose concentrations were calculated using the algorithm. These results are shown in FIG. 5. FIG. 5 is a graph showing the relationship between the known glucose concentrations in the standard specimens and the glucose concentrations in the standard specimens calculated using the algorithm. In FIG. 5, an open diamond (◇) shows the result of the Ht 29%, an open square (□) shows the result of the Ht 41%, and an open triangle (△) shows the result of the Ht 55%. As shown in FIG. 5, it was found that the glucose concentrations could be calculated very accurately for any of the standard specimens, On the other hand, as a comparative example, the glucose concentrations were calculated using the measurement results obtained after 10 seconds from the voltage application (the second-10 currents ($A_{10}$)) without correcting the Ht value. Specifically, the glucose concentrations were calculated based on the correlation equation shown in FIG. 2. The results are shown in FIG. 6. As shown in FIG. 6, the current value was varied depending on the Ht value. Thus, it was necessary to calculate the glucose concentration separately with respect to each Ht value.

INDUSTRIAL APPLICABILITY

As described above, according to the present invention, the influence of the Ht value on the measurement of a target component can be corrected with reference to the relationship between amounts of the target component and a plurality of signals corresponding thereto, thereby allowing the amount of the target component in the erythrocyte-containing specimen to be measured more accurately. Thus, it can be said that the present invention is very useful in the fields of analysis, clinical practice, etc.

The invention claimed is:

1. A method for measuring a target component in an erythrocyte-containing specimen with a biosensor that comprises an electrode and a detecting portion, comprising the steps of:
   acquiring a plurality of electrical signals derived from the target component in the erythrocyte-containing specimen with the biosensor by continuously applying a constant voltage to the electrode, thereby acquiring the plurality of electrical signals at a plurality of predetermined time points in a single application of voltage at the detecting portion; and
   determining an amount of the target component in the specimen based on the plurality of electrical signals with reference to the relationship between the amounts of the target component and the plurality of signals corresponding thereto.
2. The measurement method according to claim 1, wherein the relationship between the amounts of the target component and the plurality of signals corresponding thereto is provided with regard to different Ht values prior to measurement.

3. The measurement method according to claim 1, wherein the plurality of signals are signals acquired at two pre-determined time points.

4. The measurement method according to claim 1, wherein the plurality of signals are signals acquired at a time interval of 1 to 20 seconds.

5. The measurement method according to claim 1, wherein the plurality of signals are signals that can be detected by electrochemical measurement.

6. The measurement method according to claim 1, wherein the plurality of signals are signals that can be detected by a working electrode as a detecting portion of the biosensor.

7. The measurement method according to claim 1, wherein the plurality of signals are signals acquired up until second 20, assuming that a time point at which signal generation becomes possible is second 0.

8. The measurement method according to claim 1, wherein the plurality of signals are signals based on a redox reaction with the target component.

9. The measurement method according to claim 8, wherein the redox reaction is a reaction using an oxidoreductase and a mediator.

10. The measurement method according to claim 1, wherein the relationship between the amounts of the target component and the plurality of signals corresponding thereto with regard to different Ht values is a regression equation determined by the step of:
(X) acquiring a plurality of signals with regard to a target component concentration series of each of standard specimens having different Ht values,
determining a correlation equation between the plurality of signals with regard to each of the standard specimens,
selecting any one of the standard specimens as a reference specimen showing a reference Ht value,
setting the correlation equation of the selected reference specimen as a reference correlation equation, and
determining a regression equation for converging the correlation equations of the respective standard specimens to the reference correlation equation.

11. The measurement method according to claim 10, wherein
a plurality of corrected signals are determined from the plurality of electrical signals, and
the amount of the target component in the specimen is determined from the plurality of corrected signals with reference to a calibration equation determined by the step of:
(Y) acquiring a plurality of signals with regard to the target component concentration series of the reference specimen showing the reference Ht value, and
determining, as the calibration equation, a correlation equation between the plurality of signals and amounts of the target component in the reference specimen.

12. The measurement method according to claim 1, wherein the erythrocyte-containing specimen is whole blood.

13. The measurement method according to claim 1, wherein the target component is at least one selected from the group consisting of glucose, C-reactive protein (CRP), HbA1c, thyroid-stimulating hormone (TSH), FT3, FT4, hCG, HBs antigen, HBc antibody, HCV antibody, TY antigen, antistreptolysin O (ASO), type IV collagen, matrix metalloproteinase (MMP-3), PIVAK-II, α1 microglobulin, β1 microglobulin, amyloid A (SAA), elastase 1, basic fetoprotein (BFP), candida antigen, granulocyte elastase in cervical mucus, digoxin, cystatin C, factor XIII, urinary transferring, syphilis, hyaluronic acid, fibrin monomer complex (SFMC), von Willbrand factor (factor VIII antigen), protein S, rheumatoid factor (RF), IgD, α1 acid glycoprotein (α1AG), α1 antitrypsin (α1AT), α2 macroglobulin, albumin (Alb), ceruloplasmin (Cp), haptoglobin (Hp), prealbumin, retinol-binding protein (RBP), β1C/β1A globulin (C3), β1E globulin (C4), IgA, IgG, IgM, β lipoprotein (β-LP), apoprotein A-I, apoprotein A-II, apoprotein B, apoprotein C-II, apoprotein C-III, apoprotein E, transferring (Tf), urinary albumin, plasminogen (PLG), lipoprotein (a) (LP (a)), lactate, low density lipid, high density lipid and triglyceride.

* * * * *